(12) United States Patent
Spotila

(10) Patent No.: US 6,762,023 B1
(45) Date of Patent: Jul. 13, 2004

(54) METHODS FOR IDENTIFYING INDIVIDUALS AT RISK OF DEVELOPING OSTEOPOROSIS

(75) Inventor: Loretta D. Spotila, Haddonfield, NJ (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 09/856,937

(22) PCT Filed: Nov. 30, 1999

(86) PCT No.: PCT/US99/28403

§ 371 (c)(1),
(2), (4) Date: Aug. 15, 2001

(87) PCT Pub. No.: WO00/32826

PCT Pub. Date: Jun. 8, 2000

Related U.S. Application Data

(60) Provisional application No. 60/110,268, filed on Nov. 30, 1998.

(51) Int. Cl.[7] .......................... C12Q 1/68; C12P 19/34; C07H 21/04
(52) U.S. Cl. ..................... 435/6; 435/91.2; 536/23.5; 536/24.31; 536/25.32
(58) Field of Search .......................... 435/6, 91.2, 194, 435/810; 536/23.5, 24.31, 25.32, 24.33

(56) References Cited

U.S. PATENT DOCUMENTS

| | | | |
|---|---|---|---|
| 5,698,399 A | 12/1997 | Duff et al. | 435/6 |
| 5,766,585 A | 6/1998 | Evans et al. | 424/93.21 |
| 5,837,832 A | 11/1998 | Chee et al. | 536/22.1 |
| 5,948,638 A | 9/1999 | Lin et al. | 435/69.1 |

OTHER PUBLICATIONS

Kaufman, B.A. et al. A complex single strand conformational polymorphism (SSCP) in the tumor necrosis factor receptor 2 (TNFR2) gene on chromosome 1p36.2. Human Molecular Genetics 2(6):824 (1993).*

New England Biolabs 1992 Catalog, New England Biolabs, Inc., p. 101 (1992).*

Ahern, H. Biochemical, reagent kits offer scientists good return on investment. The Scientist 9(15):20 (Jul. 1995).*

Beltinger, C.P. Physical mapping and genomic structure of the human TNFR2 gene. Genomics 35:94–100 (1996).*

GenCore database, N–Geneseq; ID No. Q10956. EP 417, 563 A (Hoffman–La Roche AG) (Mar. 1991).*

GenCore database, N–Geneseq; ID No. Q10907. AU 9058976 A (Synergen Inc.) (Jan. 1991).*

Beltinger et al., "Physical Mapping and Genomic Structure of the Human TNFR2 Gene", *Genomics* 1996 35 (1):94–100.

* cited by examiner

*Primary Examiner*—Diana B. Johannsen
(74) *Attorney, Agent, or Firm*—Licata & Tyrrell P.C.

(57) ABSTRACT

Methods and kits for identifying individuals at risk of developing osteoporosis are provided. These methods and kits are based on detecting the presence of polymorphisms in the tumor necrosis factor alpha 2 receptor gene associated with low bone density and the risk of developing osteoporosis.

2 Claims, No Drawings

METHODS FOR IDENTIFYING INDIVIDUALS AT RISK OF DEVELOPING OSTEOPOROSIS

This application is the national stage of international application PCT/US99/28403, filed Nov. 30, 1999, which claims the benefit under 35 U.S.C. 119(e) of U.S. provisional application No. 60/110,268, filed Nov. 30, 1998.

INTRODUCTION

This invention was made in the course of research sponsored by the National Institutes of Health. The U.S. Government may have certain rights in this invention.

BACKGROUND OF THE INVENTION

Osteoporosis is a disabling condition characterized by low bone density and fragile bones. The term "osteoporosis", encompasses diseases of many different etiologies that all result in a reduction in the mass of bone per unit volume. Osteoporosis can be seen without association with other disease (idiopathic) and also in conjunction with other diseases (e.g., rheumatoid arthritis, diabetes, calcium deficiency). The decreased bone mass characteristic of the disease is not due to a decrease in the ratio of mineral to organic phase of bone, nor to any known abnormality in the mineral or organic matter of bone. Histological changes seen include a decrease in cortical thickness and a decrease in the number and size of the trabeculae of cancellous bone. Osteoporosis is the most common of all metabolic bone diseases and is seen commonly in the elderly.

Since bone mass is decreased in osteoporosis, the rate of bone resorption exceeds that of bone formation. There is a normal age-related loss of bone mass in adults. However, this age-related loss of bone begins earlier and proceeds more rapidly in women. The reasons for the age-related bone loss are not known, although risk factors identified have included race (white women being at greatest risk), sex (females), sedentary lifestyle, and less muscular development. Other factors associated with risk of developing osteoporosis include early menopause, smoking, and excessive alcohol consumption.

Diagnosis of osteoporosis is most often done in conjunction with a study of bone density by radiography. Although clinical laboratory tests such as levels of calcium and phosphorus in blood can be examined, these measures are usually normal in osteoporotic patients. Only about 20% of postmenopausal women with osteoporosis exhibit hypercalciuria, or increased excretion of calcium in urine. Therefore, such laboratory findings are not indicative of the presence of disease, and clearly would not be indicative of risk of developing disease. To date, the prediction of risk of developing disease relies on family history of the disease. However, no genetic test is currently available to screen individuals.

The ethnic differences shown to exist in the propensity to develop osteoporosis have led researchers to believe that genetic factors play a dominant role in the etiology of this disease. Several genes have been shown to be associated with low bone density and research has focused on identifying those genes that may act as markers of disease. Common allelic variations of the vitamin D receptor gene have been found to be associated with decreased bone density in certain populations, including premenopausal women and young girls (Wood, R. J. and Fleet, J. C. *Ann. Rev. Nutrit.* 1998 18:233–258). Bone mineral density has also been associated with genetic variation in the estrogen receptor gene, both by itself and in conjunction with variations in the vitamin D receptor gene (Willing et al. *J. Bone Min. Res.* 1998 13:695–705). In Japanese women, the HLA-A*24-B*07-DRB*01halotype has been linked to low peak bone mass (Tsuji et al. *Hum. Immunol.* 1998 59:243–249). A variant of the gene encoding transforming growth factor-beta 1 has also been associated with low bone mass in osteoporotic women and with low bone mass and increased bone turnover in normal women (Langdahl et al. *Bone* 1997 20:289–294). A polymorphism of the COLIAL gene has been identified as a potential marker for low bone mass and vertebral fracture in women (Grant et al. *Nat. Genet.* 1996 14:203–205). However, none of these studies has examined the relationship between tumor necrosis factor alpha receptor 2 gene and osteoporosis or bone mass in women.

Devoto et al. (*Eur. J. Hum. Genet.* 1998 6:151–157) determined that there was a gene or genes on chromosome 1 of humans that was linked to low bone density. However, there are many potential genes on this chromosome that could be involved in the etiology of low bone density.

It has now been found that individuals at risk of developing osteoporosis can be identified by assessing the genotype of the tumor necrosis factor alpha receptor gene in a sample of DNA obtained form the individual. A polymorphism in the gene on chromosome 1 for tumor necrosis factor alpha receptor 2 has now been shown to be associated with low bone density.

SUMMARY OF THE INVENTION

An object of the present invention is to provide a method of screening individuals for risk of developing osteoporosis. This method is based on assessment of the genotype of the tumor necrosis factor alpha gene in a DNA sample obtained from the individual. The presence of polymorphisms at nucleotides 593, 598 and 620 in exon 10 of the tumor necrosis factor alpha 2 receptor gene is associated with low bone density.

Another object of the present invention is to provide a kit for screening individuals for risk of developing osteoporosis which comprises a means for assessing the genotype of the tumor necrosis factor alpha 2 receptor gene in an individual.

DETAILED DESCRIPTION OF THE INVENTION

In the present invention a method is provided for screening individuals for the presence of a polymorphism in the tumor necrosis factor alpha receptor 2 (TNFR2) gene. The presence of this genotype in individuals has now been shown to be associated with low bone density and the risk of developing osteoporosis. The association between TNFR2 gene and low bone density was based on the observation that there is a polymorphism in this gene at a particular region of the gene sequence. This polymorphism was identified by Kaufman et al. (*Hum. Genet.* 1994 94:418–422), however, no characterization of its nature or examination of the relationship with bone density was disclosed. In the present invention, a relationship of this polymorphism with bone density has now been identified.

In these experiments, two polymorphic sites within the TNFR-2 gene, including a microsatellite repeat within intron 4 and a three nucleotide variation in the 3'untranslated region of the gene were assayed in three groups of individuals. Test group 1 was comprised of individuals from families used for linkage analysis of the low BMD (mean bone density) trait. Test group 2 was made up of unrelated individuals from an osteoporosis clinic. The third group was made up of unrelated individuals from a general clinic population with no testing for or knowledge of their bone status. This third group was used as reference for allele frequency comparisons. The composition and mean bone density Z-scores for test groups 1 and 2 are shown in Table 1.

TABLE 1

Results of ANOVA among the males and females comprising the two test groups for age, body mass index and bone density

|  | GROUP 1 | | GROUP 2 | | P | F ratio |
|---|---|---|---|---|---|---|
|  | Male | Female | Male | Female | Value | (df) |
| Number | 22 | 44 | 12 | 81 | | |
| Age | 56.2 | 57.3 | 43.7 | 52.6 | 0.011 | 3.846 |
| (yrs ± SE) | (2.5) | (1.9) | (3.8) | (1.5) | | (3,153) |
| Body Mass | 28.4 | 25.9 | 25.0 | 24.8 | 0.084 | 2.259 |
| Index (±SE) | (1.3) | (0.9) | (1.7) | (0.6) | | (3,149) |
| Mean BMD Z-score (±SE) | | | | | | |
| L2-L4 | −0.56 | −1.17 | −1.02 | −0.99 | 0.442 | 0.901 |
|  | (0.38) | (0.21) | (0.49) | (0.14) | | (3,155) |
| Femoral neck | −0.50 | −0.74 | −0.73 | −0.74 | 0.790 | 0.348 |
|  | (0.27) | (0.13) | (0.39) | (0.09) | | (3,150) |
| Trochanter | 0.04 | −0.64 | −0.84 | −0.59 | 0.054 | 2.611 |
|  | (0.31) | (0.16) | (0.30) | (0.11) | | (3,146) |
| Ward's triangle | −0.21 | −0.76 | −0.61 | −0.70 | 0.232 | 1.446 |
|  | (0.22) | (0.16) | (0.45) | (0.11) | | (3,146) |

Only age was significantly different among the groups (p=0.011), due to the younger mean age of the males in the second group. However, ANOVA of age as the dependent variable with genotype for the two polymorphisms as class variable indicated that age was unaffected by genotype. Therefore the results of genotype testing in the two groups were pooled for subsequent analyses.

The microsatellite repeat within intron 4 of the TNFR2 gene has been reported previously to have 5 alleles (Beltinger et al. *Genomics* 1996 35:94–100). In these test groups, 6 alleles were observed with a statistically significant difference in the frequency of distribution between the two groups (p<0.025, Table 2). A total of 18 different genotypes would be expected from 6 alleles assuming Hardy-Weinberg equilibrium. The observed frequency distribution of genotypes of the intron 4 microsatellite repeat for both the test and control groups did not differ significantly from expected (Test group Chi-square=20.54, df=19, N.S.; control group Chi-square=10.08, df=19, N.S.). Comparison of the genotype distributions between the test and control groups was also not significant (Chi-square=22.46, df=19, N.S.).

The polymorphism within the 3'UTR of the TNFR2 gene was previously characterized as having 4 alleles that were identified by different banding patterns under electrophoretic conditions that detect single strand conformation differences (Kaufman et al. *Hum. Genet.* 1994 94:418–422; White et al. *Genes, Chrom., Canc.* 1993 7:102–108; and Kaufman et al. *Hum. Molec. Genet.* 1993 2:824). Using a different conformation sensitive gel technique, 5 alleles have now been resolved, each as a single band (Table 2). The allele frequency distribution was compared between the test and control groups, with no statistically significant differences. The frequency distribution of the 15 genotypes was in Hardy-Weinberg equilibrium in both groups (Test group Chi-square=8.44, df=14, N.S.; Control group Chi-square=22.57, df=14, N.S.). However, comparison of the genotype distributions for the 3'UTR polymorphism between the test and control groups was statistically significant (Chi-square=48.70, df=14, p<0.001).

TABLE 2

Allele frequency distribution for the two TNFR2 polymorphisms in test group (n = 159) compared with control group (n = 141)

|  | Intron 4 Polymorphism* | | UTR Polymorphism** | |
|---|---|---|---|---|
| Allele | Test group | Controls | Test group | Controls |
| 1 | 0.195 | 0.156 | 0.059 | 0.038 |
| 2 | 0.037 | 0.080 | 0.229 | 0.240 |
| 3 | 0.573 | 0.551 | 0.154 | 0.137 |
| 4 | 0.186 | 0.193 | 0.374 | 0.427 |
| 5 | 0.006 | 0.004 | 0.182 | 0.156 |
| 6 | 0.003 | 0.015 | NA*** | NA |

*Chi Square = 14.74, df = 5, p < 0.025
**Chi Square = 8.24, df = 4, p < 0.10
***NA = Not applicable The nature of the UTR polymorphism was established by sequencing of PCR product from individuals who had been scored as homozygous for alleles 2, 3, 4 and 5 or heterozygous for combination of allele 1 and the other four alleles. No 1/1 homozygotes were observed. The polymorphism is actually a combination of three polymorphic sites within a span of 28 nucleotides, affecting nucleotides 593, 598 and 620 of exon 10 of the TNFR2 gene (Genbank Accession #U52165; SEQ ID NO:1). The five observed alleles are defined as summarized in Table 3.

TABLE 3

Alleles of the TNFR2 UTR polymorphism as defined by nucleotide composition at three variable sites. Numbering is based on Genbank Accession #U52165

| Alleles | Nucleotide 593 | Nucleotide 598 | Nucleotide 620 |
|---|---|---|---|
| 1 | A | G | T |
| 2 | A | T | T |
| 3 | G | T | C |
| 4 | G | T | T |
| 5 | A | T | C |

Analysis of variance (ANOVA) was performed on BMD Z-scores at the spine, femoral neck, trochanter and Ward's triangle with respect to genotype at each polymorphic site (Table 4).

TABLE 4

Results of ANOVA of BMD Z-scores with genotype for each of the two TNFR2 polymorphisms as the grouping variable in the study group (n = 159)

|  | TNFR2 Polymorphism | | | |
|---|---|---|---|---|
|  | Intron 4 Microsatellite | | 3' UTR | |
|  | P value | F ratio (df) | P value | F ratio (df) |
| L2-L4 | 0.044 | 1.937 (10,146) | 0.170 | 1.386 (13,145) |
| Femoral Neck | 0.120 | 1.574 (10,141) | 0.140 | 1.459 (13,140) |
| Trochanter | 0.199 | 1.373 (10,137) | 0.127 | 1.494 (13,136) |

TABLE 4-continued

Results of ANOVA of BMD Z-scores with genotype
for each of the two TNFR2 polymorphisms as the
grouping variable in the study group (n = 159)

| | TNFR2 Polymorphism | | | |
|---|---|---|---|---|
| | Intron 4 Microsatellite | | 3' UTR | |
| | P value | F ratio (df) | P value | F ratio (df) |
| Ward's triangle | 0.199 | 1.372 (10,137) | 0.149 | 1.439 (13,136) |

No statistically significant relationship was observed (i.e. $p<0.025$). Analysis of the genotype data using Tukey-Kramer post hoc pair-wise comparisons indicated that the mean Z-score for spinal BMD of individuals having genotype 1/2 for the UTR polymorphism was significantly different from those with genotype 2/2. Analysis of genotype data for the CA polymorphism by the Tukey-Kramer test suggested no significant differences. However, when the UTR genotypes were placed in order with respect to mean spinal BMD Z-scores, it was found that the lowest mean spinal BMD occurred in the genotype groups that had allele 1, the rarest allele (Table 5).

TABLE 5

Genotypes for the TNFR2 UTR polymorphism with
frequency and mean spinal or femoral neck BMD Z-
scores for the study group

| GENO-TYPE | FREQUENCY | SPINAL BMD Z-SCORE* (Mean ± SE) | FEMORAL NECK BMD Z-SCORE** (Mean ± SE) |
|---|---|---|---|
| 1/2 | 5 | −2.814 (0.633) | −0.727 (0.469) |
| 1/5 | 4 | −1.718 (0.708) | −1.445 (0.469) |
| 1/3 | 2 | −1.345 (1.00) | −1.620 (0.663) |
| 1/4 | 8 | −1.316 (0.500) | −0.454 (0.354) |
| 3/4 | 21 | −1.225 (0.309) | −0.920 (0.215) |
| 2/3 | 7 | −1.218 (0.535) | −0.494 (0.354) |
| 2/4 | 26 | −1.124 (0.277) | −0.777 (0.184) |
| 2/5 | 13 | −0.980 (0.393) | −0.342 (0.260) |
| 3/3 | 6 | −0.778 (0.578) | −0.458 (0.419) |
| 4/4 | 23 | −0.776 (0.295) | −0.868 (0.195) |
| 3/5 | 7 | −0.750 (0.535) | −1.108 (0.354) |
| 5/5 | 8 | −0.719 (0.500) | −1.130 (0.331) |
| 4/5 | 18 | −0.684 (0.334) | −0.508 (0.221) |
| 2/2 | 11 | −0.023 (0.427) | −0.022 (0.282) |
| Total | 159 | | |

*ANOVA, $p = 0.17$, $R^2 = 0.11$
**ANOVA, $p = 0.14$, $R^2 = 0.12$

The mean femoral neck BMD Z-scores are shown for comparison, and indicate a similar trend in that the two lowest mean Z-scores occur in groups having allele 1.

Thus, these analysis show that the frequency of the rarest allele of this gene is associated with low bone density. Further, this association between the genotype of TNFR2 and bone density is statistically significant ($p=0.008$). Accordingly, assessment of the genotype of the TNFR2 gene of an individual is useful in identifying individuals with low bone density at risk for osteoporosis.

In the method of the present invention, a DNA sample is obtained from an individual. The genotype of the TNFR2 gene is then assessed to determine if the individual is at risk for developing osteoporosis. For example, detection of a polymorphisms at nucleotides 593, 598 and 620 of exon 10 of the TNFR2 gene (SEQ ID NO:1) is indicative of an individual at risk of developing osteoporosis.

The present invention also relates to diagnostic kits comprising a means for identifying individuals at risk of developing osteoporosis based on assessment of the genotype of the TNFR2 gene. In a preferred embodiment, such means are capable of detecting polymorphisms at nucleotides 593, 598 and 620 of exon 10 of the TNFR2 gene (SEQ ID NO:1). Such means can be developed routinely by those skilled in the art based upon known techniques for genotype screening such as PCR and gel electrophoresis. In one embodiment, the kit comprises primers such as exemplified by SEQ ID NO: 4 and SEQ ID NO:5 described in Example 3 herein. However, as will be obvious to those of skill in the art upon this disclosure, additional means useful in assessing the TNFR2 genotype of an individual can also be used. In a preferred embodiment, the kits of the present invention further comprise a blood collection device for obtaining a blood sample from an individual as the source of DNA for genotyping. Other sources of DNA obtained from a patient which can be genotyped via the kits and methods of the present invention include both tissue samples and other biological fluids.

Using the method and/or kits of the present invention, one of skill can screen individuals known to have a family history of low bone density and/or individuals with identified risk factors for osteoporosis and low bone density including, but not limited to, post-menopausal women and the elderly. Via these methods and kits, individuals having polymorphisms in the TNFR2 gene, and in particular polymorphisms detected at nucleotide 593, 598 and 620 of exon 10 of the TNFR2 gene (SEQ ID NO:1), can be identified as being at risk of developing osteoporosis.

The following non-limiting examples are provided to further illustrate certain aspects of the instant invention.

EXAMPLES

Example 1

Subjects

The first group of test subjects was composed of 66 individuals unrelated to each other. These individuals were either the founders of or had married into families with low BMD. The second test group of 93 individuals were also unrelated to each other and to the first group and had been referred to the McGill Bone Center by physicians for evaluation of bone status. The third group was a random general clinic population (n=141), that served as a control for allele frequency distribution in these studies.

Blood was collected from participants and DNA was isolated by standard methods. Bone densitometry was performed on individuals in the first two groups in accordance with procedures described by Devoto et al. *Eur. J. Hum. Genet.* 1998 6:151–157 and Spotila et al. *Calcif. Tissue Int.* 1996 59:235–237.

Example 2

Microsatellite Repeat in Intron 4

The PCR primers for detection of the $(CA)_{16}$ microsatellite repeat described by Beltinger et al. (*Genomics* 1996 35:94–100) were TNFR2-CAF:5'-GTGATCTGCA AGATGAACTCAC-3' (SEQ ID NO:2) and TNFR2-CAR:5'-ACACCACGTCTGATGTTTCA-3' (SEQ ID NO:3). PCR conditions were denaturation at 94.5° C. for 3 minutes; followed by 5 cycles of 94.5° C. for 30 seconds, 65.0° C. for 30 seconds, 72° C. for 30 seconds, followed by 23 cycles of 94.5° C. for 30 seconds, 55.0° C. for 30 seconds, 72.0° C. for 30 seconds; followed by 72.0° C. for 5 minutes in a Perkin Elmer Thermocycler 9600. The primer TNFR2-CAF was labeled with y-$^{32}$P-ATP using T4 polynucleotide kinase. Approximately 100–300 ng of DNA template was used with reaction components under conditions recommended by the manufacturer (Applied Biosystems).

Example 3

Polymorphism of 3' Untranslated Region

PCR primers for detection of the polymorphism within the 3'UTR of TNFR2 as described by Kaufman et al. (Hum. Genet. 1994 94:418–422) were TNFR2–7:5'-AGGACTCTGAGGCTCTTTCT-3' (SEQ ID NO:4) and TNFR2–8:5'-TCACAGAGAGTCAGGGACTT-3' (SEQ ID NO: 5). PCR conditions were denaturation at 94.5° C. for 3 minutes; followed by 28 cycles of 94.5° C. for 30 seconds, 62.0° C. for 30 seconds, 72.0° C. for 30 seconds; followed by 72.0° C. for 5 minutes. Reagents and instrumentation were the same as described for Example 2.

Using conformation sensitive gel electrophoresis (CSGE), 5 differentially migrating fragments of this PCR product were distinguished. Gel conditions and product suppliers were similar to those described by Ganguly et al. (*Proc. Natl Acad. Sci. USA* 1996 93:13721–13725) with the following modifications. Tris-taurine-EDTA running buffer was made as a 20× stock with 1.78 M Tris, 0.58 M Taurine, 4.0 mM EDTA, pH 9.0 and used at 0.5×. Formamide was deionized in batches and frozen in aliquots sufficient for a single gel. Sample loading buffer was prepared each time with 4 parts deionized formamide and 1 part loading buffer (5×=0.1% xylene cyanol, 0.1% bromophenol blue, 10 mM EDTA, 95% formamide). Standard sequencing gel plates and apparatus were used with 0.4 mm spacers. Samples were mixed with an equal volume of sample loading buffer, denatured for 5 minutes at 95° C., transferred to ice and 1.5 µl was immediately loaded. Gels were run at 350 V at room temperature for 16 to 18 hours, then dried and exposed to film. Resolution of 5 alleles was possible only when these conditions were adhered to.

Example 4

Sequence Analysis

Selected PCR fragments were sequenced according to manufacturer's recommendations using ABI 377 instrumentation and Big-Dye chemistry (Applied Biosystems, Inc. Foster City, Calif.) in order to determine the basis for the 5 alleles.

Example 5

Statistical Analysis

The two test groups were compared by ANOVA for age, body mass index and BMD Z-score at the spine, femoral neck, trochanter and Ward's triangle, and then combined for additional analyses. The frequency distribution of alleles for the two polymorphisms within the TNFR2 gene was analyzed by Chi Square. Association of bone density at the spine (L2–L4), femoral neck, trochanter and Ward's triangle with genotype for each of the two polymorphisms was evaluated by ANOVA. The BMD Z-scores at each of the anatomical sites were used as the independent variable since they were already corrected for age, gender and weight. Statistical significance was achieved at p<0.025, because of multiple testing. Pairwise comparisons of mean BMD Z-scores for the different genotypes were made for all pairs using the Tukey-Kramer post hoc test. Power analysis was performed to determine the lowest sample number required to observe a significant (p=0.025) effect of genotype on BMD. The statistical software package employed was JMP (Version 3.1, SAS Institute, Inc. Cary, N.C.).

What is claimed is:

1. A method for identifying a human individual at risk of developing osteoporosis comprising assessing the genotype of the tumor necrosis factor alpha 2 receptor (TNFR2) gene in a sample of DNA from the individual, and identifying the individual as being at risk of developing osteoporosis if the individual possesses 3' UTR allele 1 of the TNFR2 gene.

2. The method of claim 1 wherein said 3' UTR allele 1 is indicative of low bone density levels and wherein said low bone density levels are indicative of the individual being at risk of developing osteoporosis.

* * * * *

SEQUENCE LISTING

```
<160> NUMBER OF SEQ ID NOS: 5

<210> SEQ ID NO 1
<211> LENGTH: 2613
<212> TYPE: DNA
<213> ORGANISM: Homo sapien

<400> SEQUENCE: 1
tcttggtctc ggctcctggc ccagtgctct ttcccatgtg tctgaatctg catcttgggc      60 agggtccct  gggccccact cctggacccc cggactgacc cccaccccat cttgtgctta     120
gcagattctt cccctggtgg ccatgggacc caggtcaatg tcacctgcat cgtgaacgtc     180
tgtagcagct ctgaccacag ctcacagtgc tcctcccaag ccagctccac aatgggagac     240
acagattcca gcccctcgga gtccccgaag gacgagcagg tccccttctc caaggaggaa     300
tgtgcctttc ggtcacagct ggagacgcca gagaccctgc tggggagcac cgaagagaag     360
cccctgcccc ttggagtgcc tgatgctggg atgaagccca gttaaccagg ccggtgtggg     420
ctgtgtcgta gccaaggtgg gctgagccct ggcaggatga ccctgcgaag gggccctggt     480
ccttccaggc ccccaccact aggactctga ggctctttct gggccaagtt cctctagtgc     540
```

```
cctccacagc cgcagcctcc ctctgacctg caggccaaga gcagaggcag cgagttgggg      600
aaagcctctg ctgccatggt gtgtccctct cggaaggctg gctgggcatg gacgttcggg      660
gcatgctggg gcaagtccct gactctctgt gacctgcccc gcccagctgc acctgccagc      720
ctggcttctg gagcccttgg gttttttgtt tgtttgtttg tttgtttgtt tgtttctccc      780
cctgggctct gcccagctct ggcttccaga aaaccccagc atccttttct gcagaggggc      840
tttctggaga ggagggatgc tgcctgagtc acccatgaag acaggacagt gcttcagcct      900
gaggctgaga ctgcgggatg gtcctggggc tctgtgtagg gaggaggtgg cagccctgta      960
gggaacgggg tccttcaagt tagctcagga ggcttgaaaa gcatcacctc aggccaggtg     1020
cagtggctca cgcctatgat cccagcactt tgggaggctg aggcgggtgg atcacctgag     1080
gttaggagtt cgagaccagc ctggccaaca tggtaaaacc ccatctctac taaaaataca     1140
gaaattagcc gggcgtggtg gcgggcacct atagtcccag ctactcagaa gcctgaggct     1200
gggaaatcgt ttgaacccgg gaagcggagg ttgcagggag ccgagatcac gccactgcac     1260
tccagcctgg gcgacagagc gagagtctgt ctcaaaagaa aaaaaaaaa gcaccgcctc     1320
caaatgctaa cttgtccttt tgtaccatgg tgtgaaagtc agatgcccag agggcccagg     1380
caggccacca tattcagtgc tgtggcctgg gcaagataac gcacttctaa ctagaaatct     1440
gccaattttt taaaaagta agtaccactc aggccaacaa gccaacgaca aagccaaact     1500
ctgccagcca catccaaccc cccacctgcc atttgcaccc tccgccttca ctccggtgtg     1560
cctgcagccc cgcgcctcct tccttgctgt cctaggccac accatctcct ttcagggaat     1620
ttcaggaact agagatgact gagtcctcgt agccatctct ctactcctac ctcagcctag     1680
accctcctcc tcccccagag gggtgggttc tcttcccca ctccccacct tcaattcctg      1740
ggccccaaac gggctgccct gccactttgg tacatggcca gtgtgatccc aagtgccagt     1800
cttgtgtctg cgtctgtgtt gcgtgtcgtg ggtgtgtgta gccaaggtcg gtaagttgaa     1860
tggcctgcct tgaagccact gaagctggga ttcctcccca ttagagtcag ccttccccct     1920
cccagggcca gggccctgca gaggggaaac cagtgtagcc ttgcccggat tctgggagga     1980
agcaggttga ggggctcctg gaaaggctca gtctcaggag catggggata aaggagaagg     2040
catgaaattg tctagcagag caggggcagg gtgataaatt gttgataaat tccactggac     2100
ttgagcttgg cagctgaact attggagggt gggagagccc agccattacc atggagacaa     2160
gaagggtttt ccaccctgga atcaagatgt cagactggct ggctgcagtg acgtgcacct     2220
gtactcagga ggctgagggg aggatcactg gagcccagga gtttgaggct gcagcgagct     2280
atgatcgcgc cactcactc cagcctgagc aacagagtga gaccctgtct cttaaagaaa      2340
aaaaaagtca gactgctggg actggccagg tttctgccca cattgacccc acatgaggac     2400
atgatggagc gcacctgccc cctggtggac agtcctggga gaacctcagg cttccttggc     2460
atcacagggc agagccggga agcgatgaat ttggagactc tgtggggcct tggttccctt     2520
gtgtgtgtgt gttgatccca agacaatgaa agtttgcact gtatgctgga cggcattcct     2580
gcttatcaat aaacctgttt gttttaaaaa aaa                                   2613
```

<210> SEQ ID NO 2
<211> LENGTH: 22
<212> TYPE: DNA
<213> ORGANISM: Artificial Sequence
<220> FEATURE:
<223> OTHER INFORMATION: Synthetic

<400> SEQUENCE: 2

-continued

```
gtgatctgca agatgaactc ac                                        22

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
acaccacgtc tgatgtttca                                           20

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
aggactctga ggctctttct                                           20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
tcacagagag tcagggactt                                           20
```